Figure 1A:
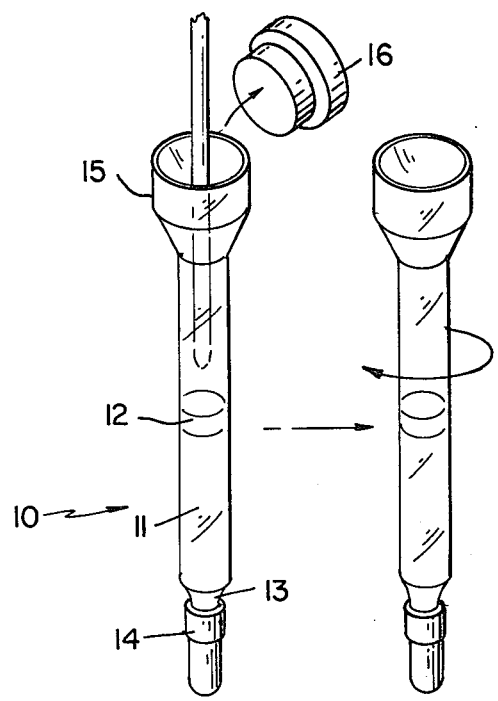

United States Patent [19]

Bulbenko

[11] 4,243,534
[45] Jan. 6, 1981

[54] BLOOD SEPARATION

[75] Inventor: George F. Bulbenko, Langhorne, Pa.

[73] Assignee: Becton, Dickinson and Company, Paramus, N.J.

[21] Appl. No.: 6,450

[22] Filed: Jan. 25, 1979

[51] Int. Cl.³ .................................................. B01D 15/08
[52] U.S. Cl. ................................ 210/656; 23/230 B; 210/198.2
[58] Field of Search ............ 210/31 C, 198, DIG. 23; 23/230 B

[56] References Cited

U.S. PATENT DOCUMENTS 4,142,858  3/1979  Acuff .................................. 210/31 C

OTHER PUBLICATIONS

Introduction to Modern Liquid Chromatography by Snyder and Kirkland, p. 292, Wiley Interscience Pub., 1974.

Primary Examiner—John Adee
Attorney, Agent, or Firm—Louis E. Marn; Elliot M. Olstein

[57] ABSTRACT

A chromatographic column includes an adsorbant for separating blood components and a lysing agent for hemolyzing the blood whereby a whole blood sample can be applied to the column to effect hemolysis and blood separation in one operation. The invention is particularly employed for analysis of fast running hemoglobin (glycosylated hemoglobin.)

21 Claims, 3 Drawing Figures

BLOOD SEPARATION

This invention relates to blood separation, and more particularly to blood separation by column chromatography. This invention further relates to an improved device and process for the determination of glycosylated hemoglobin.

Column chromatography has been employed for separating blood into constituent components. In many cases, a whole blood sample must be lysed prior to being introduced into the chromatographic column for effecting the desired separation.

Thus, for example, hemoglobin $A_{1c}$ (Hb $A_{1c}$) formed by glycosylation of hemoglobin A by glucose in vivo has been suggested as an indicator of diabetic control. Hb $A_{1c}$ along with minor components Hb $A_{1a}$ and Hb $A_{1b}$, whose exact compositions are undetermined, can be separated from the major hemoglobin component (Hb $A_o$) by virtue of its fast moving through an ion exchange column Schnek, A. G. and Schroeder, W. A., *J. Am. Chem. Soc.*, 83. 1472 (1961), Trivelli, L. A. Ranney, H. M., and Lal, H. T., *New England J. Med.*, 284, 353 (1971). In order to effect separation of the glycosylated hemoglobin (also referred to as total fast hemoglobin) from the major hemoglobin component, the whole blood sample is lysed to form a hemolysate and the hemolysate is introduced into the chromatographic column.

In accordance with the present invention there is provided a new and improved device and process for effecting separation of blood components by column chromatography which does not require separate lysing of a whole blood sample. More particularly, in accordance with the present invention, there is provided a chromatographic column for separating blood components which includes a lysing agent for hemolyzing whole blood whereby a whole blood sample can be directly added to the column, with the blood being hemolysed on the column. In this manner, separate hemolysis of the blood is eliminated.

The present invention will be further described with respect to the separation of fast hemoglobins from the major hemoglobin component; however the scope of the invention is not to be limited to such separation.

In the determination of glycosylated hemoglobins in accordance with the present invention, there is provided a chromatographic column which includes an absorption agent for adsorbing hemoglobin. As known in the art such adsorption agents adsorb hemoglobin, and subsequently the glycosylated hemoglobins can be separated from the main hemoglobin component by appropriate elution. As representative of such adsorption agents, there may be mentioned: clays, modified cellulose; e.g., carboxyl modified cellulose, ion exchange resins, both cationic and anionic; etc., with ion exchange resins being preferred.

The selection of a suitable adsorbant for effecting the separation is deemed to be well within the scope of those skilled in the art from the teachings herein.

The column chromatography is effected at a pH effective for providing the adsorption of hemoglobin and subsequent elution of the glycosylated hemoglobin from the main hemoglobin. In general, the pH from 5.0 to 10.0, and preferably from 6.0 to 8.0. It is to be understood that higher and lower pH values could be used; however, lower values may require a longer eluting time, whereas at higher values material may pass through the column too rapidly. In accordance with a preferred embodiment of the present invention, the adsorbant is pre-conditioned in a buffer suitable for providing the pH at which the chromatographic separation is to be effected. In this manner, the column is ready for use.

In accordance with the invention, the column includes a lysing agent for effecting hemolysis of whole blood. Such lysing agents are however in the art, and as representative examples of suitable lysing agents, there may be mentioned: surfactants (anionic, cationic, non-ionic); saponin, etc. The selection of a suitable lysing agent is deemed to be well within the scope of those skilled in the art from the teachings herein.

The lysing agent on the column is suitably buffered to the pH at which the separation is to be effected so as not to upset the operation of the column and is present in an amount suitable for effecting hemolysis of the whole blood sample to be placed on the column, with the quantity thereof being insufficient to elute the glycosylated hemoglobins from the column, whereby in the initial step the glycosylated and main hemoglobin component, subsequent to hemolysis, are adsorbed on the column. Thus, in accordance with the present invention, the chromatographic column includes a suitable adsorbing agent for effecting separation of the glycosylated hemoglobins from the main hemoglobin component and a lysing agent for hemolyzing the blood. A whole blood sample is then introduced into the column and mixed with the lysing agent, which is present in a liquid which lies above the adsorption agent to effect hemolysis of the blood sample. The hemolysate is then allowed to flow onto the adsorption agent to effect adsorption of the hemoglobin.

The glycosylated hemoglobin can then be eluted from the column in order to separate the glycosylated hemoglobin from the main hemoglobin component. Such elution may be effected by procedures generally known in the art. For example, a liquid comprised of the same components as the liquid lysing agent originally present in the column may be passed through the column in a quantity effective for eluting glycosylated hemoglobin without elution of the main hemoglobin component. Alternatively, elution can be effected with a liquid at a pH greater than the pH at which the initial adsorption is conducted or having an ionic strength greater than the liquid used for placing the hemoglobin on the column. Thus, the quantity, pH and ionic strength of the eluting liquid are coordinated to effect elution of glycosylated hemoglobin without eluting the main hemoglobin component. The selection of a suitable eluting agent is within the scope of those skilled in the art from the teachings herein.

In accordance with the present invention, there is provided a procedure for the quantitative determination of glycosylated hemoglobin. In accordance with the procedure, a whole blood sample is added to the column containing lysing agent and adsorbant to effect hemolysis of the blood sample. The hemolysate is then allowed to run onto the adsorbant, to effect adsorption of the hemoglobin. The glycosylated hemoglobins are then eluted from the column and the amount of total glycosylated hemoglobin is determined from the eluate; e.g., by use of a spectrophotometer. The total glycosylated hemoglobin is expressed as a percent of total hemoglobin (independently determined).

The invention will be further described with respect to the accompanying drawings, wherein:

FIGS. 1 A–C illustrate a preferred embodiment of the chromatographic device of the present invention.

Referring to the drawings, there is shown a chromatographic column, generally indicated as 10, which includes a suitable adsorbant for effecting separation of fast running hemoglobins from the main hemoglobin component, and generally indicated as 11. The adsorbant is preferably an ion exchange resin, which has been buffered to the operating pH; e.g., pH 6.80, by a suitable buffer, e.g., phosphate buffer. The column further includes a lysing agent for effecting hemolysis of whole blood which is on top of the adsorbant and is generally indicated as 12. The lysing agent is preferably buffered to the operating pH of the column. The total amount of liquid above the adsorbing agent is an amount which will not elute hemoglobin from the adsorbing agent. Thus, for example, a representative column would include about 1.2 ml of adsorbing agent, in particular weakly acidic polymethacrylate resin crosslinked with divinyl benzene (200–400 mesh) equilibrated in sodium phosphate buffer, pH 6.80, and above the adsorbing agent 0.5 ml of liquid, including lysing agent; in particular, aqueous sodium phosphate buffer, 41.6 mmol/liter (pH6.8), containing potassium cyanide (10 mmol/liter) and as lysing agent 0.2% polyethylene glycol p-isooctyl-phenyl ether (Triton X-100). The column includes an outlet tip 13 closed by a suitable closure member such as removable cap 14 and an inlet 15 closed by a closure member, such as stopper 16.

As should be apparent, the column 10 is capable of being used for effecting separation of glycosylated hemoglobins from a whole blood sample for quantitative determination of glycosylated hemoglobin.

Figure 1B:
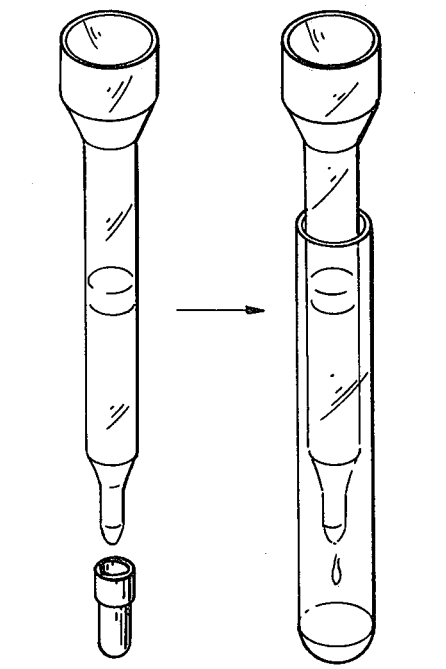

For example, as shown in FIG. 1A stopper 16 is removed and 10 ul of a whole blood sample can be added to the column followed by mixing for about one minute to effect hemolysis of the whole blood.

Cap 14 is then removed from the outlet tip 13 and hemolysate flows onto the adsorbing agent to adsorb the hemoglobin with unadsorbed components flowing into a test tube (FIG. 1B), which is discarded when dripping stops.

Figure 1C:
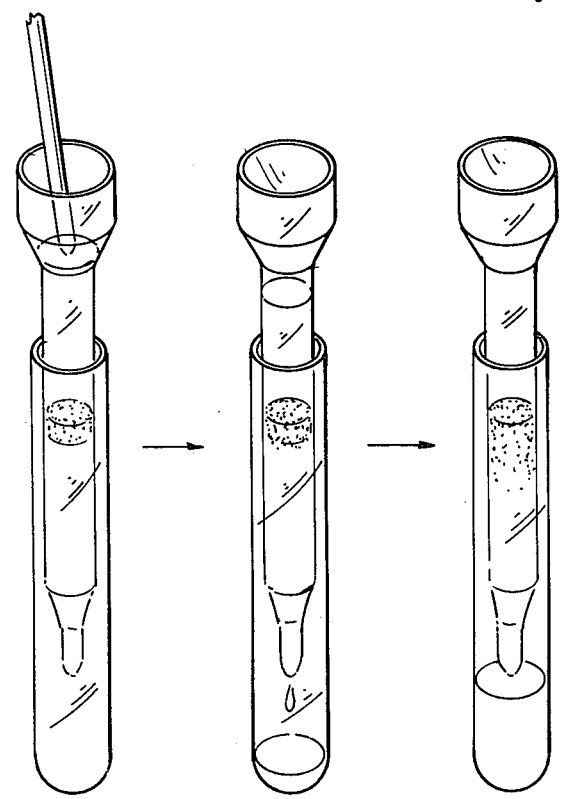

Eluting agent (about 3 ml) (identical to the liquid 12 except that lysing agent concentration is 0.1%) is then introduced into the column and eluate, containing the glycosylated hemoglobins, is collected in a clean tube (FIG. 1C). The total amount of glycosylated hemoglobin can be determined by reading the adsorbance of the eluate at 415 nm in a spectrophotometer zeroed against water.

The glycosylated hemoglobins may be expressed as a percent of total hemoglobin. The total hemoglobin may be determined by mixing 10 ul of whole blood sample with the hereinabove described eluting buffer, which contains a lysing agent, to effect hemolysis of the blood. 20 ml of distilled water is added to the hemolysate and total hemoglobin determined by reading adsorbance at 415 nm in a spectrophotometer. The percent is determined as follows:

$$\text{Glycosylated Hemoglobin} = \frac{\text{Absorbance glycosylated Hb}}{\text{Absorbance total Hb} \times 6.83}$$

wherein 6.83 is the dilution factor (3 ml of eluate at 20.5 ml of total Hb sample).

The determined percent of fast running hemoglobins may then be employed, for example, as an indicator of diabetic control. Thus, a normal range for fast running hemoglobins, expressed as a percent, would be in the order of 6.6 to 8.9%. Values above such normal range would provide an indication of increased blood glucose levels and relate to diabetic condition.

Although the embodiment has been described with reference to the lysing agent and eluting agent being the same composition, as should be apparent, the respective agents can be different compositions and can be at different pH values.

Similarly, although the preferred embodiment has been described with reference to chromatographic separation of glycosylated hemoglobins, the invention is also applicable to the separation of other blood components in which whole blood is hemolysed prior to the separation, e.g., separation of hemoglobin $A_2$, hemoglobin F and S, etc.

It is also to be understood that the invention could be employed for separating hemoglobin from other blood components, e.g., glucose. All of the hemoglobin would remain on the column, with other components passing through the column or subsequently eluted therefrom.

The present invention is particularly advantageous in that it permits separation of blood components by column chromatography without the necessity of effecting separate hemolysis of whole blood. In addition, the present invention provides a device and procedure for the analysis of glycosylated hemoglobin. These and other advantages should be apparent to those skilled in the art from the teachings herein.

Numerous modifications and variations of the present invention are possible in light of the above teachings and, therefore, within the scope of the appended claims the invention may be practised otherwise than as particularly described.

I claim:

1. A chromatographic device for separating blood components, comprising:
    a chromatographic column, said column including an adsorbing agent for adsorbing blood components which is preconditioned in a buffer to the operating pH for chromatographic separation, a liquid comprising a blood lysing agent which lies above said adsorbing agent in an amount sufficient to hemolyze a whole blood sample which is to be subsequently introduced into the column; and closure means for the column to maintain the liquid and adsorbing agent in the column prior to use thereof, whereby upon use of the column a whole blood sample introduced into the column is hemolyzed in the column by the lysing agent prior to flowing through the adsorbing agent.

2. The device of claim 1 wherein the adsorbing agent is preconditioned in a buffer to the operating pH for chromatographic separation.

3. The device of claim 1 wherein the adsorbing agent is an agent for adsorbing hemoglobin.

4. The device of claim 3 wherein the absorbing agent is an ion exchange resin.

5. The device of claim 3 wherein the adsorption agent is a modified cellulose.

6. A chromatographic device for separation of glycosylated hemoglobin from the main hemoglobin component, comprising:
    a chromatographic column said column including an adsorbing agent for adsorbing hemoglobin, said adsorbing agent being equilibrated to an operating pH for separating glycosylated hemoglobin from the main hemoglobin component, said pH being from 5.0 to 10.0, a liquid above the adsorbing agent comprising a blood lysing agent in an amount sufficient to hemolyze a whole blood sample which is to be subsequently introduced into the column, and closure means for the column to maintain the liquid and adsorbing agent in the column prior to use thereof, whereby upon use of the column a whole blood sample introduced into the column is hemolyzed in the column by the lysing agent prior to flowing through the adsorbing agent.

7. The device of claim 6 wherein the adsorbing agent is an ion exchange resin.

8. The device of claim 6 wherein the adsorbing agent is a modified cellulose.

9. The device of claim 6 wherein the lysing agent is a surfactant dissolved in water.

10. The device of claim 6 wherein the lysing agent is saponin.

11. The device of claim 6 wherein the lysing agent is buffered to the operating pH.

12. The device of claim 11 wherein the pH is from 6.0 to 8.0.

13. The device of claim 12 wherein the adsorbing agent is weakly acidic polymethacrylate resin crosslinked with divinyl benzene equilibrated to a pH of 6.8.

14. The device of claim 13 wherein the lysing agent is a surfactant dissolved in water.

15. A process for determining the amount of glycosylated hemoglobins in a blood sample, comprising:
introducing a whole blood sample into a chromatographic column, including an adsorbing agent for adsorbing hemoglobin and a liquid comprising a blood lysing agent which lies above said adsorbing agent in an amount sufficient to hemolyze a whole blood sample, said liquid comprising the blood lysing agent being present above said adsorbing agent prior to introduction of the whole blood sample into the column, said adsorbing agent and said liquid comprising the blood lysing agent being buffered to an operating pH for separating glycosylated hemoglobin, prior to introduction of the whole blood sample, said pH being from 5.0 to 10.0;
hemolyzing the whole blood sample in the column with the lysing agent to produce a hemolysate;
passing the hemolysate into the adsorbing agent to adsorb hemoglobin;
eluting glycosylated hemoglobins from the adsorbing agent to produce an eluate; and
determining the amount of glycosylated hemoglobins in the eluate.

16. The process of claim 15 wherein said adsorbing agent and said liquid comprising the blood lysing agent are buffered to an operating pH for separating glycosylated hemoglobin, prior to introduction of the whole blood sample, said pH being from 5.0 to 10.0.

17. The process of claim 15 wherein the lysing agent is a surfactant.

18. The process of claim 15 wherein the lysing agent is saponin.

19. The process of claim 15 wherein the adsorbing agent is weakly acidic polymethacrylate resin crosslinked with divinyl benzene equilibrated to a pH of 6.8.

20. The process of claim 19 wherein the lysing agent is a surfactant.

21. The process of claim 15 wherein the determined glycosylated hemoglobins are expressed as a percent of total hemoglobin in the blood sample.

* * * * *